(12) United States Patent
Philips et al.

(10) Patent No.: US 8,945,851 B2
(45) Date of Patent: Feb. 3, 2015

(54) QUANTITATIVE ASSAY FOR MEMBRANE ASSOCIATION OF PROTEINS

(75) Inventors: Mark R. Philips, New York, NY (US); Nicole Fehrenbacher, New York, NY (US); Joseph Wynne, New York, NY (US)

(73) Assignee: New York University, New York, NY (US)

( * ) Notice: Subject to any disclaimer, the term of this patent is extended or adjusted under 35 U.S.C. 154(b) by 433 days.

(21) Appl. No.: 13/222,620

(22) Filed: Aug. 31, 2011

(65) Prior Publication Data

US 2012/0066782 A1    Mar. 15, 2012

Related U.S. Application Data

(60) Provisional application No. 61/378,692, filed on Aug. 31, 2010.

(51) Int. Cl.
*C12Q 1/68*    (2006.01)

(52) U.S. Cl.
CPC ........... *C12Q 1/6897* (2013.01); *A01K 2217/00* (2013.01); *A01K 2227/105* (2013.01); *C07K 2319/71* (2013.01); *C07K 2319/80* (2013.01); *C07K 2319/915* (2013.01)
USPC ..... 435/6.15; 435/6.18; 435/320.1; 536/23.4; 536/25.32; 536/24.1

(58) Field of Classification Search
None
See application file for complete search history.

(56) References Cited

U.S. PATENT DOCUMENTS 5,525,490 A * 6/1996 Erickson et al. ................ 435/29
6,506,889 B1 * 1/2003 Han et al. ...................... 536/23.1

OTHER PUBLICATIONS

Bivona et al., "PKC Regulates a Farnesyl-Electrostatic Switch on K-Ras That Promotes Its Association With Bcl-XL on Mitochondria and Induces Apoptosis," Mol. Cell 21:481-493 (2006).
Ogura et al., "Adaptation of GAL4 Activators for GAL4 Enhancer Trapping in Zebrafish," Developmental Dynamics 238:641-655 (2009).
Yeung et al., "Receptor Activation Alters Inner Surface Potential During Phagocytosis," Science 313:347-351 (2006).
Mark R. Philips, "Development of Anti-Cancer Drugs that Target K-Ras," BioAccelerate NYC Prize Pre-proposal, 4 pages, submitted Sep. 1, 2010.

* cited by examiner

*Primary Examiner* — Jim Ketter
(74) *Attorney, Agent, or Firm* — LeclairRyan, a Professional Corporation

(57) ABSTRACT

The present invention relates to a kit for detection of association of a peripheral cellular membrane binding protein with cellular membranes in living cells and methods thereof. The kit includes a first nucleic acid construct comprising a first nucleic acid molecule encoding a first fusion protein comprising a peripheral cellular membrane binding protein or membrane binding domain thereof operatively coupled to DNA binding and transactivation domains of a naturally occurring or chimeric transcription factor and a first promoter operatively associated with the first nucleic acid molecule. A second nucleic acid construct comprises a second nucleic acid molecule encoding a reporter protein and a second promoter responsive to the DNA binding and transactivation domains of the first fusion protein. The second promoter is operatively associated with the second nucleic acid molecule. Activation of the second promoter results in expression of the reporter protein. Also disclosed is a transgenic non-human animal.

32 Claims, 3 Drawing Sheets

QUANTITATIVE ASSAY FOR MEMBRANE ASSOCIATION OF PROTEINS

This application claims the benefit of U.S. Provisional Patent Application Ser. No. 61/378,692, filed Aug. 31, 2010, which is hereby incorporated by reference in its entirety.

FIELD OF THE INVENTION

The present invention relates to kits and methods for detection of association of a peripheral cellular membrane binding protein with cellular membranes in living cells.

BACKGROUND OF THE INVENTION

Some membrane proteins are not membrane-spanning but are attached to the plasma membrane via membrane anchors or interactions with integral membrane proteins. Membrane anchors are covalently joined to a protein post-translationally and include such moieties as prenyl, myristyl, and glycosylphosphatidyl inositol (GPI) groups. Membrane localization of peripheral and anchored proteins is important for their function in processes such as receptor-mediated signal transduction. For example, prenylation of Ras is required for its localization to the plasma membrane and for its normal and oncogenic functions in signal transduction.

Ras genes are members of the Ras supergene family of genes, present in various species, including humans and rodents. This supergene family consists of 50 or more genes that encode structurally related proteins which possess a guanine triphosphate binding site and intrinsic guanine triphosphatase (GTPase) activity. Many members of this superfamily of proteins are critical for diverse intracellular signaling pathways. The Ras subfamily in humans of this supergene family includes 36 genes that encode 39 proteins (Wennerberg et al., "The Ras Superfamily at a Glance," *J. Cell Science* 118(5):843-846 (2005)). Among these are the H-Ras, K-Ras (also known as Kras2), N-Ras, Rap, Rheb and Ral genes. The chromosomal locations of each of the human Ras genes is known in the art.

Ras proteins are attractive targets for anti-cancer drugs because they are believed to be involved in at least 30% of human cancers. Ras proteins must associate with cellular membranes in order to function and, therefore, one strategy for developing anti-Ras drugs is to inhibit membrane targeting of the Ras proteins. Central to the mechanism whereby three of the four iso forms of Ras associate with membranes is their post-translational modification with a farnesyl lipid and, in the case of N-Ras and H-Ras, one or two palmitate lipids.

Although mammalian genomes contain three Ras genes, mutations in K-Ras are most frequently associated with human cancer (Bos, "Ras Oncogenes in Human Cancer: A Review," *Cancer Res.* 49:4682-4689 (1989)). Therefore, properties that are specific to K-Ras are of particular significance to cancer biologists since they might be exploited in the development of anti-cancer drugs. The differential biology of Ras iso forms is generated, in large part, by distinct membrane targeting sequences. Membrane association of all Ras isoforms requires prenylation (i.e., farnesylation), proteolysis, and carboxyl methylation of a C-terminal CAAX (SEQ ID NO:1) motif (where C stands for cysteine, A for an aliphatic amino acid and X for any amino acid). Plasma membrane targeting of the principal splice variant of K-Ras also requires a unique polybasic region adjacent to the CAAX motif (Hancock et al., "A Polybasic Domain or Palmitoylation is Required in Addition to the CAAX Motif to Localize p21$^{ras}$ to the Plasma Membrane," *Cell* 63:133-139 (1990); Jackson et al., "Polylysine Domain of K-Ras 4B Protein is Crucial for Malignant Transformation," *Proc. Natl. Acad. Sci. USA* 91:12730-12734 (1994); Choy et al., "Endomembrane Trafficking of Ras: The CAAX Motif Targets Proteins to the ER and Golgi," *Cell* 98:69-80 (1999)).

K-Ras thus falls into a broad class of proteins that are anchored to the cytoplasmic face of the plasma membrane by virtue of post-translational modification with lipids that act in conjunction with polybasic stretches of polypeptide. Whereas the lipid moieties are thought to insert into the phospholipid bilayer, the polybasic regions are believed to associate with the anionic head groups of inner leaflet phospho lipids (Leventis et al., "Lipid-Binding Characteristics of the Polybasic Carboxy-Terminal Sequence of K-Ras4B," *Biochemistry* 37:7640-7648 (1998)). Considering the significance of this class of proteins, there is a need for information about the mechanism of cellular membrane interaction and control of such interaction.

The present invention is directed to overcoming these and other deficiencies in the art.

SUMMARY OF THE INVENTION

One aspect of the present invention relates to a kit for detection of association of a peripheral cellular membrane binding protein with cellular membranes in living cells. The kit includes a first nucleic acid construct comprising a first nucleic acid molecule encoding a first fusion protein comprising a peripheral cellular membrane binding protein or membrane binding domain thereof operatively coupled to DNA binding and transactivation domains of a naturally occurring or chimeric transcription factor and a first promoter operatively associated with the first nucleic acid molecule. The kit also includes a second nucleic acid construct comprising a second nucleic acid molecule encoding a reporter protein and a second promoter responsive to the DNA binding and transactivation domains of the first fusion protein. The second promoter is operatively associated with the second nucleic acid molecule, whereby activation of the second promoter results in expression of the reporter protein.

Another aspect of the present invention is directed to a method for detection of association of a peripheral cellular membrane binding protein with a cellular membrane in living cells. This method involves providing a kit comprising a first nucleic acid construct, which includes a first nucleic acid molecule encoding a fusion protein comprising a peripheral cellular membrane binding protein or membrane binding domain thereof operatively coupled to DNA binding and transactivation domains of a naturally occurring or chimeric transcription factor and a first promoter operatively associated with the first nucleic acid molecule. The kit also includes a second nucleic acid construct comprising a second nucleic acid molecule encoding a reporter protein and a second promoter responsive to the DNA binding and transactivation domains. The second promoter is operatively associated with the second nucleic acid molecule, whereby activation of the second promoter results in expression of the reporter protein. The method also involves transforming a first set of the living cells with the first and second nucleic acid constructs. Expression of the reporter protein is detected in the first set of transformed living cells. The first set of transformed living cells expressing the reporter protein are identified as having a lack or inhibition of peripheral membrane protein association with a cellular membrane of the living cells.

In order for the translation product of the first nucleic acid to activate the promoter of the second nucleic acid, that product must have free access to the nucleus of the cell. Association with cellular membranes retards access to the nucleus such that the efficiency of the first nucleic acid in activating the second nucleic acid is inversely proportional to the efficiency of membrane association and the system thereby reports dissociation from membranes either constitutively from the outset of expression or conditionally. Thus, the cells expressing the reporter protein (i.e., the product of the second nucleic acid construct) are identified as those for which membrane association of the product of the first nucleic acid construct either does not occur in the first place or is inhibited in living cells.

A further aspect of the present invention relates to a transgenic non-human animal. The transgenic non-human animal comprises a first nucleic acid construct comprising a first nucleic acid molecule encoding a first fusion protein comprising a peripheral cellular membrane binding protein or membrane binding domain thereof operatively coupled to DNA binding and transactivation domains of a naturally occurring or chimeric transcription factor and a first promoter operatively associated with the first nucleic acid molecule. The transgenic non-human animal also comprises a second nucleic acid construct comprising a second nucleic acid molecule encoding a reporter protein and a second promoter responsive to the DNA binding and transactivation domains of the first fusion protein. The second promoter is operatively associated with the second nucleic acid molecule, whereby activation of the second promoter results in expression of the reporter protein.

DETAILED DESCRIPTION OF THE INVENTION

Figure 1:
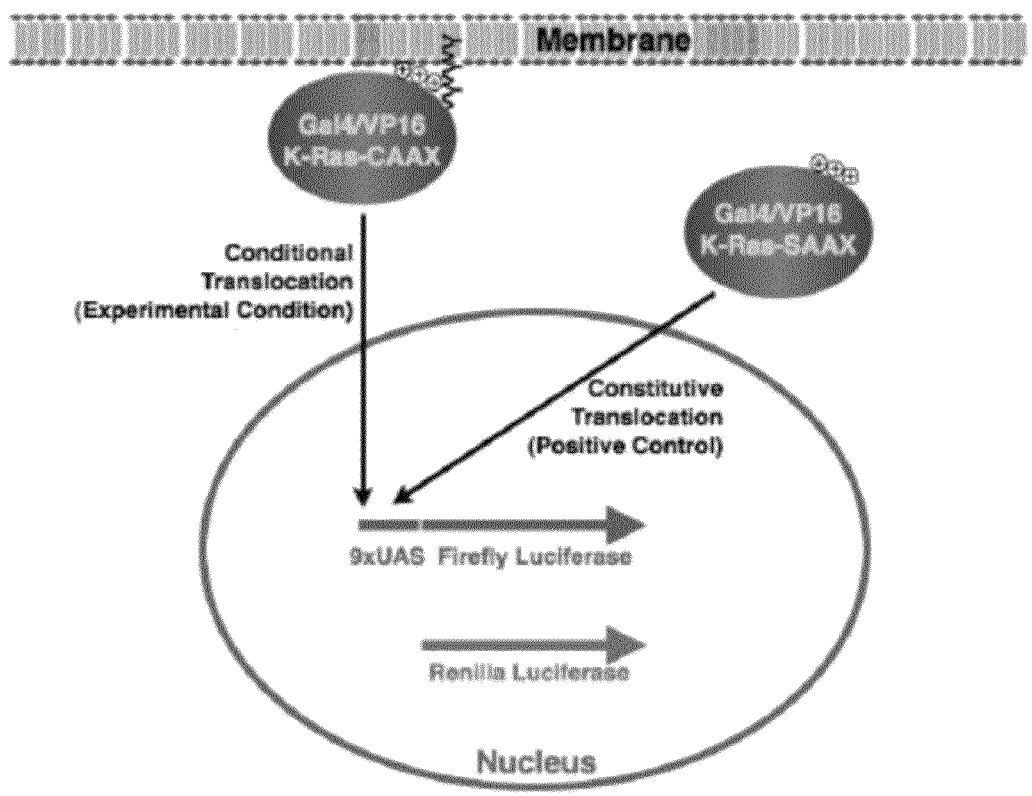
FIG. 1 is a schematic illustration of a K-Ras membrane release assay according to one embodiment of the present invention. The Gal4 DNA binding domain linked to a VP16 transactivation domain is fused to the N-terminus of K-Ras with or without the C189S "SAAX" (SEQ ID NO:2) mutation that eliminates farnesylation and membrane targeting. Gal4/VP16-K-Ras-SAAX is free to leak into the nucleus and drive expression of firefly luciferase off of a UAS promoter. This serves as the positive control for soluble K-Ras. Gal4/VP16-K-Ras-CAAX is targeted to the membrane and, therefore, unable to leak into the nucleus. When a condition is applied that releases Gal4/VP16-K-Ras-CAAX from membranes, some of the released protein leaks into the nucleus and activates firefly luciferase. Along with the Gal4/VP16-K-Ras and UAS-firefly luciferase, the cells are also transfected with a plasmid encoding renilla luciferase that serves as a control for transfection efficiency, protein expression, and cell viability.

A first aspect of the present invention relates to a kit for detection of association of a peripheral cellular membrane binding protein with cellular membranes in living cells. The kit includes a first nucleic acid construct comprising a first nucleic acid molecule encoding a first fusion protein comprising a peripheral cellular membrane binding protein or membrane binding domain thereof operatively coupled to DNA binding and transactivation domains of a naturally occurring or chimeric transcription factor and a first promoter operatively associated with the first nucleic acid molecule. The kit also includes a second nucleic acid construct comprising a second nucleic acid molecule encoding a reporter protein and a second promoter responsive to the DNA binding and transactivation domains of the first fusion protein. The second promoter is operatively associated with the second nucleic acid molecule, whereby activation of the second promoter results in expression of the reporter protein.

It should be understood that descriptions with respect to embodiments of the first aspect of the present invention are to apply to, and may be embodiments of, all aspects of the present invention.

According to the present invention, the peripheral cellular membrane binding proteins may include GTPase proteins. GTP-binding proteins (also called GTPases because of the GTP hydrolysis that they catalyze) constitute a large family of proteins that all have a similar GTP-binding globular domain. When its bound GTP is hydrolyzed to GDP, this domain undergoes a conformational change that inactivates the protein. Examples of GTPase proteins for use with the methods of the present invention include, without limitation, K-Ras (including both splice variants K-Ras4A and K-Ras4B), Rap1, and Rac1.

In one embodiment, the kit according to this aspect of the present invention is a kit for detection of association of the peripheral cellular membrane binding protein K-Ras with cellular membranes. K-Ras falls into a broad class of proteins that are anchored to the cytoplasmic face of the plasma membrane by virtue of post-translational modification with lipids that act in conjunction with polybasic stretches of polypeptide. Whereas the lipid moieties are thought to insert into the phospholipid bilayer, the polybasic regions are believed to associate with the anionic head groups of inner leaflet phospholipids. Membrane association of all Ras isoforms requires prenylation (i.e., farnesylation), proteolysis, and carboxyl methylation of a C-terminal CAAX motif. Plasma membrane targeting of K-Ras also requires a unique polybasic region of about 20 amino acids adjacent to the CAAX motif. K-Ras is a protein having the amino acid sequence of SEQ ID NO:3, set forth in GenBank Accession No. NP_004976.2, as follows:

```
MTEYKLVVVG AGGVGKSALT IQLIQNHFVD EYDPTIEDSY RKQVVIDGET CLLDILDTAG

QEEYSAMRDQ YMRTGEGFLC VFAINNTKSF EDIHHYREQI KRVKDSEDVP MVLVGNKCDL

PSRTVDTKQA QDLARSYGIP FIETSAKTRQ GVDDAFYTLV REIRKHKEKM SKDGKKKKKK

SKTKCVIM
```

In one embodiment, K-Ras is encoded by the nucleotide sequence of SEQ ID NO:4, as follows:

```
ATGACTGAAT ATAAACTTGT GGTAGTTGGA GCTGGTGGCG TAGGCAAGAG TGCCTTGACG

ATACAGCTAA TTCAGAATCA TTTTGTGGAC GAATATGATC CAACAATAGA GGATTCCTAC

AGGAAGCAAG TAGTAATTGA TGGAGAAACC TGTCTCTTGG ATATTCTCGA CACAGCAGGT

CAAGAGGAGT ACAGTGCAAT GAGGGACCAG TACATGAGGA CTGGGGAGGG CTTTCTTTGT

GTATTTGCCA TAAATAATAC TAAATCATTT GAAGATATTC ACCATTATAG AGAACAAATT

AAAAGAGTTA AGGACTCTGA AGATGTACCT ATGGTCCTAG TAGGAAATAA ATGTGATTTG

CCTTCTAGAA CAGTAGACAC AAAACAGGCT CAGGACTTAG CAAGAAGTTA TGGAATTCCT

TTTATTGAAA CATCAGCAAA GACAAGACAG GGTGTTGATG ATGCCTTCTA TACATTAGTT

CGAGAAATTC GAAAACATAA AGAAAAGATG AGCAAAGATG GTAAAAAGAA GAAAAAGAAG

TCAAAGACAA AGTGTGTAAT TATGTAA
```

In another embodiment, the GTPase protein is a Rap1 protein (e.g., a Rap1a protein). Rap1a is a ubiquitously expressed GTPase in the Ras family that regulates a wide variety of cellular processes, including lymphocyte adhesion, and through activation of B-Raf, is involved in cellular transformation.

In yet another embodiment, the GTPase protein is a Rac1 protein. Rac1, belonging to the Rho small GTPase family, regulates the actin cytoskeleton but also other cellular processes including oncogenic transformation and metastasis. Rac1 has been shown to be involved in the regulation of cell-cell adhesion.

This aspect of the present invention may involve detection of association of other peripheral membrane proteins with cellular membranes, including, without limitation, GTPases of the Ras superfamily that end with a CAAX sequence including N-Ras, H-Ras, K-Ras4A/4B, R-Ras, M-Ras, TC21, RasD1/2, Di-Ras1/2, Rap1/2, RalA/B, Rheb, Rad, Rem, Rag, RhoA-G, Rac1-3, Cdc42, Wrch1/2, Rnd1/2, TC10, and the gamma subunits of heterotrimeric G proteins, as well as GTPases that do not include a CAAX motif such as Arf, Arl, Rab, Sar, and Rit. These also include Src family kinases that associate with membranes via an SH4 domain, as well as a wide assortment of proteins that associate with membranes by virtue of conserved domains that include, but are not limited to, Plextrin homology (PH), PX, and Bar domains, as well as peripheral membrane proteins that associate with intrinsic membrane proteins via interaction domains such as SH2, PTB, SH3, and PZD.

As used herein, the phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operatively coupled" or "operatively associated" refer to the situation in which a first nucleic acid sequence is placed in a functional relationship with a second nucleic acid sequence. For instance, a promoter is operatively coupled or operatively associated to a coding sequence if the promoter affects the transcription or expression of the coding sequence. Operatively coupled or operatively associated DNA sequences may be in close proximity or contiguous and, where necessary to join two protein coding regions, in the same reading frame.

In one embodiment, the nucleic acid constructs according to the present invention are in expression vectors, as described in further detail infra.

As used herein, the term "DNA-binding domain" encompasses a small (about 150 amino acids) peptide sequence of a DNA-binding protein, up to the entire length of a DNA-binding protein, so long as the DNA-binding domain functions to associate with a particular response element (e.g., has a specific DNA binding activity towards a DNA sequence, e.g., a promoter). For example, in certain embodiments of the present invention, the DNA binding domain refers to the portion of the fusion protein that interacts with the corresponding second promoter on the second nucleic acid construct according to the present invention. The DNA binding domain can be from Yeast or from another organism that can include, but is not limited to, a bacteria, a human, a mouse, a rat, and the like.

In one embodiment, the DNA binding domain comprises Gal4.

In one embodiment, the second promoter that is responsive to the DNA binding and transactivation domains comprises a multimerized upstream activation sequence ("UAS") recognized by Gal4.

As used herein, a "transactivation domain" refers to a polypeptide, which acts to activate transcription of a target nucleotide (e.g., reporter gene). The transactivation domain refers to the portion of the fusion protein that interacts with the corresponding promoter sequence on the reporter polynucleotide. The transactivation domain and the promoter sequence on the reporter polynucleotide are selected so that they interact in an appropriate manner for the assay according to the present invention.

Examples of transactivation domains that may be used in embodiments of the present invention include, but are not limited to, the transactivation domain of HSV virion protein VP16 or certain parts thereof, adenovirus E1A, Epstein-Barr virus EBNA 2, yeast Gal4, mammalian Sp1, Oct1 and Oct2, NF-Kappa B, and the like.

In one particular embodiment, the transactivation domain is the transactivation domain of the HSV virion protein VP16.

In certain embodiments according to the present invention, the DNA binding and transactivation domains are operatively coupled or operatively associated. In one particular embodiment of the present invention, VP16 is coupled to Gal4.

In accordance with embodiments of the present invention, a "reporter protein" or "detectable label" refers to a reporter molecule or enzyme that is capable of generating a measurable signal and is covalently or noncovalently joined to a polynucleotide or polypeptide. In one iteration, the protein is an enzyme, and can be detected by assaying the enzymatic reaction catalyzed by the enzyme, e.g., development of a chromogenic product or light. For example, the reporter gene can be luciferase and the activity can be detected as the production of photons (light) or the reporter can be β-galactosidease and its presence can be detected by the blue color produced when X-gal reagent is added as a substrate. Other enzymes suitable for use as reporters include, but are not limited to, chloramphenicol transferase, horseradish peroxidase, and alkaline phosphatase. In another iteration, the reporter can be a fluorescent protein such as green fluorescent protein, red fluorescent protein, or any of the muteins thereof. In one embodiment, the protein encoded by the reporter gene is luminescent (fluorescent or phosphorescent). In a specific embodiment, the protein is luciferase. In another specific embodiment, the protein is green fluorescent protein.

In one embodiment of this aspect of the present invention, the kit further comprises a control nucleic acid construct. The control nucleic acid construct includes a third nucleic acid molecule encoding a further fusion protein that includes DNA binding and transactivation domains operatively coupled to a domain that will not bind to a cellular membrane. The control nucleic acid construct also includes the first promoter operatively associated with the third nucleic acid molecule.

In one embodiment, the first, second, and control nucleic acid constructs are in expression vectors, as described in further detail infra.

The domain that will not bind to a cellular membrane may be the peripheral cellular membrane binding protein or membrane binding domain thereof that has been modified or mutated to eliminate its ability to target or bind to the cellular membrane.

In one embodiment, the peripheral cellular membrane binding protein or membrane binding domain thereof is a K-Ras protein or C-terminal fragment thereof containing a "CAAX" sequence, which is modified by farnesylation, proteolysis and carboxyl methylation and thereby targets the protein to cellular membranes, while the further fusion protein is a K-Ras protein lacking a "CAAX" which eliminates post-translational modification and membrane targeting.

In one particular embodiment, the K-Ras protein lacking "CAAX" is a K-Ras protein with a C185S "SAAX" mutation.

It will be understood that kits according to the present invention can further include appropriate buffers and reagents known in the art for administering various combinations of the components listed above to a host cell or host organism.

Another aspect of the present invention is directed to a method for detection of association of a peripheral cellular membrane binding protein with a cellular membrane in living cells. This method involves providing a kit comprising a first nucleic acid construct, which includes a first nucleic acid molecule encoding a fusion protein comprising a peripheral cellular membrane binding protein or membrane binding domain thereof operatively coupled to DNA binding and transactivation domains of a naturally occurring or chimeric transcription factor and a first promoter operatively associated with the first nucleic acid molecule. The kit also includes a second nucleic acid construct comprising a second nucleic acid molecule encoding a reporter protein and a second promoter responsive to the DNA binding and transactivation domains. The second promoter is operatively associated with the second nucleic acid molecule, whereby activation of the second promoter results in expression of the reporter protein. The method also involves transforming a first set of the living cells with the first and second nucleic acid constructs. Expression of the reporter protein is detected in the transformed living cells. The first set of transformed living cells expressing the reporter protein is identified as having a lack or inhibition of peripheral membrane protein association with a cellular membrane of the living cells.

In carrying out the method of detection of the present invention, nucleic acid constructs are used to transform living cells such that expression of a protein can be detected. To this end, a nucleic acid molecule encoding the above-noted proteins can be introduced into an expression system of choice using conventional recombinant technology.

Generally, this involves inserting the nucleic acid molecule into an expression system to which the molecule is heterologous (i.e., not normally present). The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression system or vector in proper sense (5'→3') orientation and correct reading frame. The vector contains the necessary elements for the transcription and translation of the inserted protein-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, including vaccinia virus, adenovirus, and retroviruses, including lentivirus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express the protein-encoding sequence in a cell. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon (ATG) to provide a ribosome binding site. Thus, any SD-ATG combination that can be utilized by host cell ribosomes may be employed. Such combinations include, but are not limited to, the SD-ATG combination from the cro gene or the N gene of coliphage lambda, or from the *E. coli* tryptophan E, D, C, B, or A genes. Additionally, any SD-ATG combination produced by recombinant DNA or other techniques involving incorporation of synthetic nucleotides may be used.

Depending on the vector system and host utilized, any number of suitable transcription and/or translation elements, including constitutive, inducible, and repressible promoters, as well as minimal 5' promoter elements may be used.

The nucleic acid construct(s), a promoter molecule of choice, a suitable 3' regulatory region, and if desired, a reporter gene, are incorporated into a vector-expression system of choice to prepare a nucleic acid construct using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

The nucleic acid molecule encoding a nucleic acid construct according to the present invention is inserted into a vector in the sense (i.e., 5'→3') direction, such that the open reading frame is properly oriented for the expression of the encoded protein under the control of a promoter of choice. Single or multiple nucleic acids may be ligated into an appropriate vector in this way, under the control of a suitable promoter, to prepare a nucleic acid construct.

Once the isolated nucleic acid molecule encoding the protein or polypeptide has been cloned into an expression system, it is ready to be incorporated into a host cell. Recombinant molecules can be introduced into cells via transformation, particularly transduction, conjugation, lipofection, protoplast fusion, mobilization, particle bombardment, or electroporation. The DNA sequences are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, fungi, mammalian cells, insect cells, plant cells, and the like.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, puromycin, streptomycin, spectinomycin, tetracycline, chloramphenicol, and the like. Similarly, "reporter genes," which encode enzymes providing for production of an identifiable compound identifiable, or other markers which indicate relevant information regarding the outcome of gene delivery, are suitable. For example, various luminescent or phosphorescent reporter genes are also appropriate, such that the presence of the heterologous gene may be ascertained visually.

In one embodiment of this aspect of the present invention, the kit further comprises a control nucleic acid construct. The control nucleic acid construct includes a third nucleic acid molecule encoding a further fusion protein that includes DNA binding and transactivation domains operatively coupled to a domain that will not bind to a cellular membrane. The control nucleic acid construct also includes the first promoter operatively associated with the third nucleic acid molecule. The method according to this embodiment of the present invention further includes transforming a second set of the living cells with the second nucleic acid construct and the control nucleic acid construct, resulting in constitutive activation of the second promoter and constitutive expression of the reporter protein. Expression of the reporter protein is detected in the second set of transformed living cells. Expression levels of the reporter protein in the first set of transformed living cells is compared to that in the second set of transformed living cells.

In another embodiment, the method according to this aspect of the present invention further involves providing a plurality of candidate agents for inhibition of peripheral membrane protein association with a cellular membrane of the living cells. This method also involves contacting each of the plurality of candidate agents with the transformed living cells and identifying candidate compounds which increase or decrease expression of the reporter protein as having potential application as treating conditions mediated by peripheral membrane protein association or dissociation with a cellular membrane.

In one embodiment, the candidate agents or compounds according to the present invention are small molecule compounds. In another embodiment of the present invention, the candidate compound is an siRNA molecule.

In one embodiment, the peripheral membrane protein is K-Ras.

In one embodiment, this method is carried out to detect increased expression of the reporter protein and identify candidate compounds having potential application as an anti-K-Ras drug.

In another embodiment, the method is carried out to detect increased expression of the reporter protein and identify candidate compounds having potential application as an anti-cancer drug. Thus, for example, a potential anti-Ras drug is a compound that dislodges Ras from the membrane or prevents membrane association and, therefore, leads to an increase in reporter expression.

In yet another embodiment, the method further comprises quantifying inhibition of peripheral membrane protein association with a cellular membrane of the living cells by comparing the first and second levels of expression of the reporter protein. In this embodiment, the level of expression of the reporter protein from the first set of transformed cells is compared to that of the second set of transformed cells. Different expression levels may indicate activity of a candidate compound to have activity as a disease-fighting or -preventing agent.

In yet a further embodiment, the method according to the present invention further comprises quantifying inhibition of peripheral membrane protein association with a cellular membrane of the living cells based on reporter protein expression level.

Quantifying the inhibition of peripheral membrane protein association with a cellular membrane of the living cells based on reporter protein expression level can be carried out by comparison to the control level (as noted above) or to a standard or known value. This known value can be set by reference to a pre-correlated value with a particular level of inhibition.

Methods of the present invention may be carried out in vivo or in vitro. In all aspects of the present invention, transforming "a cell" or "living cells" can be carried out as desired, including, but not limited to, transforming cells in culture. Animals (e.g., mice, rats or other mammals comprising "cells" or "living cells" according to the present invention) may also be transformed according to the present invention and, in turn, injected with candidate agents or compounds to be identified.

Another aspect of the present invention relates to a transgenic non-human animal. The transgenic non-human animal comprises a first nucleic acid construct comprising a first nucleic acid molecule encoding a first fusion protein comprising a peripheral cellular membrane binding protein or membrane binding domain thereof operatively coupled to DNA binding and transactivation domains of a naturally occurring or chimeric transcription factor and a first promoter operatively associated with the first nucleic acid molecule. The transgenic non-human animal also comprises a second nucleic acid construct comprising a second nucleic acid molecule encoding a reporter protein and a second promoter responsive to the DNA binding and transactivation domains of the first fusion protein. The second promoter is operatively associated with the second nucleic acid molecule, whereby activation of the second promoter results in expression of the reporter protein.

In one embodiment, the non-human transgenic animal is a rodent. For example, the transgenic animal may be a mouse or a rat.

The transgenic animal comprises exogenous DNA incorporated into the animal's cells to effect a permanent or transient genetic change, preferably a permanent genetic change. Permanent genetic change is generally achieved by introduction of the DNA into the genome of the cell. Vectors for stable integration include plasmids, retroviruses and other animal viruses, YACS, and the like. Generally, transgenic animals are non-human mammals, most typically mice.

The exogenous nucleic acid sequence may be present as an extrachromosomal element or stably integrated in all or a portion of the animal's cells, especially in germ cells.

Unless otherwise indicated, a transgenic animal includes stable changes to the GERMLINE sequence. During the initial construction of the animal, chimeric animals (chimeras) are generated, in which a subset of cells has the altered genome. Chimeras may then be bred to generate offspring heterozygous for the transgene. Male and female heterozygotes may then be bred to generate homozygous transgenic animals.

Typically, transgenic animals are generated using transgenes from a different species or transgenes with an altered nucleic acid sequence. For example, a human gene may be introduced as a transgene into the genome of a mouse or other animal. The introduced gene may be a wild-type gene, naturally occurring polymorphism, or a genetically manipulated sequence, for example having deletions, substitutions, or insertions in the coding or non-coding regions.

For example, an introduced transgene may include genes corresponding to the nucleic acid constructs of the present invention, which may become functional via complementation or reconstitution when exposed to appropriate test proteins or, alternatively, which may become non-functional when exposed to a particular test protein that blocks phosphorylation. Such a transgene, when introduced into a transgenic animal or cells in culture, is useful for testing potential therapeutic agents known or believed to interact with a particular target protein implicated in a disease or disorder (e.g., the cellular membrane binding function of K-Ras or other peripheral membrane binding proteins). Where the introduced gene is a coding sequence, it is usually operably linked to a promoter, which may be constitutive or inducible, and other regulatory sequences required for expression in the host animal as described herein.

Transgenic animals can be produced by any suitable method known in the art, such as manipulation of embryos, embryonic stem cells, etc. Transgenic animals may be made through homologous recombination, where the endogenous locus is altered. Alternatively, a nucleic acid construct is randomly integrated into the genome. Vectors for stable integration include plasmids, retroviruses and other animal viruses, YACS, and the like.

Numerous methods for preparing transgenic animals are now known and others will likely be developed. See, e.g., U.S. Pat. Nos. 6,252,131; 6,455,757; 6,028,245; and 5,766,879, all of which are hereby incorporated by reference in their entirety. Any method that produces a transgenic animal expressing a reporter gene following complementation or reconstitution is suitable for use in the present invention. The microinjection technique is particularly useful for incorporating transgenes into the genome without the accompanying removal of other genes.

EXAMPLES

Example 1

The Quantitative K-Ras Membrane Association Assay is Sensitive to Mutation of the K-Ras Membrane Targeting Sequence, Prenyltransferase Inhibitors, and Silencing of the Common α Subunit of Farnesyltransferase and Geranylgeranyltransferase I A membrane release assay according to the present invention is shown in FIG. 1. The Gal4 DNA binding domain linked to a VP16 transactivation domain is fused to the N-terminus of K-Ras with or without the C189S "SAAX" mutation that eliminates farnesylation and membrane targeting. Gal4/VP16-K-Ras-SAAX is free to leak into the nucleus and drive expression of firefly luciferase off of a UAS promoter. This serves as the positive control for soluble K-Ras and establishes the upper limit of the read out. Gal4/VP16-K-Ras-CAAX is targeted to the membrane and, therefore, unable to leak into the nucleus. When a condition is applied that releases Gal4/VP16-K-Ras-CAAX from membranes, some of the released protein leaks into the nucleus and activates firefly luciferase. Along with the Gal4/VP16-K-Ras and UAS-firefly luciferase, the cells are also transfected with a plasmid encoding renilla luciferase that serves as a control for transfection efficiency, protein expression and cell viability.

Figure 2:
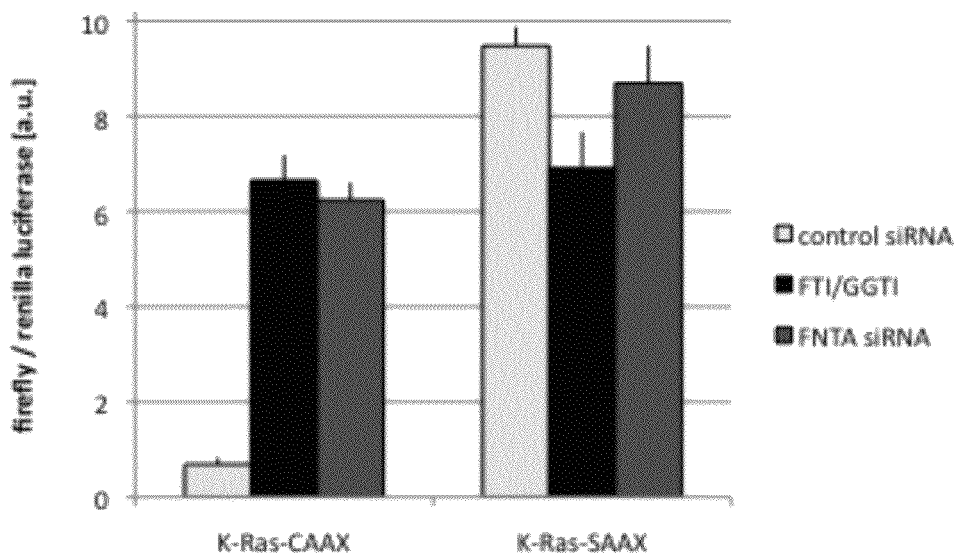
FIG. 2 is a bar graph showing results that demonstrate that the quantitative K-Ras membrane association assay, according to one embodiment of the present invention, is sensitive to mutation of the K-Ras membrane targeting sequence, prenyltransferase inhibitors, and silencing of the common α subunit of farnesyltransferase ("FTase") and geranylgeranyltransferase I ("GGTase I"). HeLa cells transfected with VP16/Gal4 fused to K-Ras4B with a native membrane targeting sequence (CAAX), or one lacking the cysteine required for prenylation (SAAX), along with UAS-firefly luciferase and renilla luciferase expression vectors, were treated without or with a cocktail of farnesyl transferase inhibitor ("FTI") and geranylgeranyltransferase inhibitor ("GGTI") or an siRNA targeting the common α subunit of FTase and GGTase I ("FNTA"). Twenty-four hours after transfection, the cells were lysed and the activities of the two luciferase enzymes were measured with a plate reader following addition of dual luciferase reagents.

FIG. 2 is a bar graph showing results that demonstrate that the quantitative K-Ras membrane association assay, according to one embodiment of the present invention, is sensitive to mutation of the K-Ras membrane targeting sequence, prenyltransferase inhibitors, and silencing of the common α subunit of FTase and GGTase I. HeLa cells transfected with VP16/Gal4 fused to K-Ras4B with a native membrane targeting sequence (CAAX), or one lacking the cysteine required for prenylation (SAAX), along with UAS-firefly luciferase and renilla luciferase expression vectors, were treated without or with a cocktail of FTI and GGTI or an siRNA targeting the common α subunit of FNTA. Twenty-four hours after transfection, the cells were lysed and the activities of the two luciferase enzymes were measured with a plate reader following addition of dual luciferase reagents.

Figure 3:
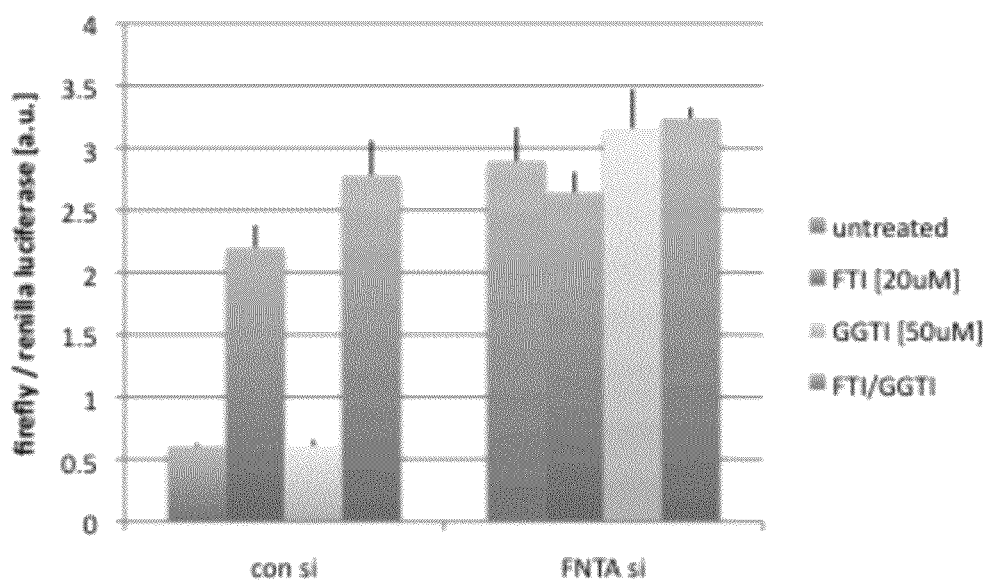
FIG. 3 is a bar graph showing results that demonstrate that the quantitative K-Ras membrane association assay according to one embodiment of the present invention is sensitive to prenyltransferase inhibitors and silencing of the common α subunit of FTase and GGTase I. HeLa cells transfected with VP16/Gal4 fused to K-Ras4B, along with UAS-firefly luciferase and renilla luciferase expression vectors and a non-targeting siRNA (Con) or an siRNA targeting the common α subunit of FTase and GGTase I, FNTA, were treated with or without FTI and/or GGTI. Twenty-four hours after transfection, the cells were lysed and the activities of the two luciferase enzymes were measured with a plate reader following addition of dual luciferase reagents.

HeLa cells transfected with VP16/Gal4 fused to K-Ras4B, along with UAS-firefly luciferase and renilla luciferase expression vectors and a non-targeting siRNA (Con) or an siRNA targeting the common α subunit of FTase and GGTase I, FNTA, were treated with or without FTI and/or GGTI. Twenty-four hours after transfection, the cells were lysed and the activities of the two luciferase enzymes were measured with a plate reader following addition of dual luciferase reagents. FIG. 3 is a bar graph showing results that demonstrate that the quantitative K-Ras membrane association assay is sensitive to prenyltransferase inhibitors and silencing of the common α subunit of FTase and GGTase I.

Example 2

Figure 4:
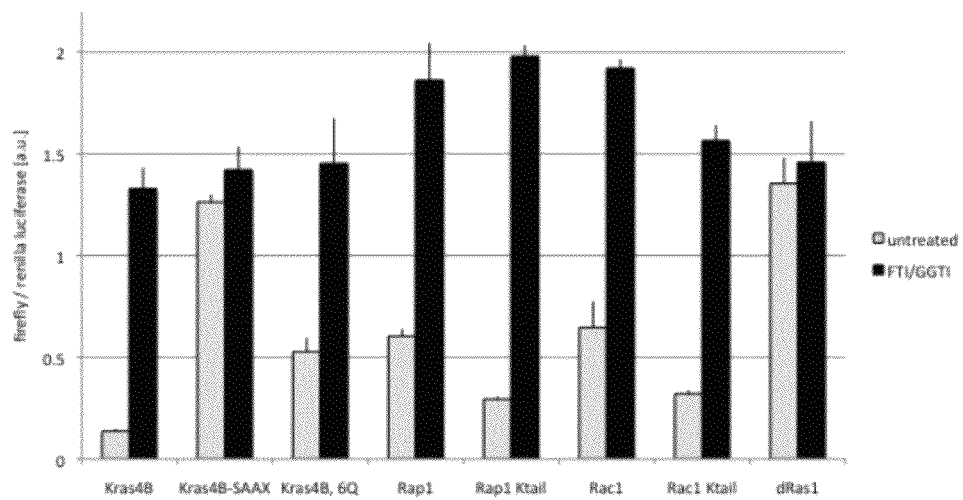
FIG. 4 is a bar graph showing results that confirm that the assay of the present invention is suitable for small GTPases other than K-Ras. HeLa cells were transfected for 24 hrs in 96-wells with Gal4-VP16 chimeric proteins as indicated and left untreated or incubated with FTI/GGTI, which reveals the dynamic range of the assay system for each indicated chimera. Treatment with FTI/GGTI leads to a significant increase in basal luciferase for both Rap1 and Rac1, suggesting this assay is suitable for a broad-range of small GTPases with various membrane anchors. K-Ras4B, 6Q refers to a mutation of 6 consecutive lysines to glutamines in the C-terminal region of K-Ras (amino acids 175-180). This leads to a neutralization of 6 positive charges and, therefore, less membrane attachment of K-Ras. Rap1Ktail and Rac1Ktail refer to the exchange of the native C-terminal membrane-localizing region for that of K-Ras4B. Such a switch in C-terminal regions leads to a higher membrane affinity of Rap1 and Rac1 that is comparable to wild-type K-Ras. DRas1 refers to *Drosophila* Ras that is inefficiently prenylated due to a lysine in the A1 position of the CAAX sequence of DRas1. Hence, the basal luciferase levels are comparable to those of FTI/GGTI co-treatment. Values are averages of quadruplicate ratios of firefly over renilla luciferase activity +/−SDs.

The Quantitative K-Ras Membrane Association Assay is Suitable for Peripheral Membrane Proteins Other than K-Ras HeLa cells were transfected for 24 hrs in 96-wells with Gal4-VP16 chimeric proteins as indicated and left untreated or incubated with FTI/GGTI, which reveals the dynamic range of the assay system for each indicated chimera. Treatment with FTI/GGTI leads to a significant increase in basal luciferase for both Rap1 and Rac1, suggesting this assay is suitable for a broad-range of small GTPases with various membrane anchors. K-Ras4B, 6Q refers to a mutation of 6 consecutive lysines to glutamines in the C-terminal region of K-Ras (amino acids 175-180). This leads to a neutralization of 6 positive charges and, therefore, less membrane attachment of K-Ras. Rap1Ktail and Rac1Ktail refer to the exchange of the native C-terminal membrane-localizing region for that of K-Ras4B. Such a switch in C-terminal regions leads to a higher membrane affinity of Rap1 and Rac1 that is comparable to wild type K-Ras. DRas1 refers to *Drosophila* Ras that is inefficiently prenylated due to a lysine in the A1 position of the CAAX sequence of DRas1. Hence, the basal luciferase levels are comparable to those of FTI/GGTI co-treatment. FIG. 4 is a bar graph showing results that confirm that the present assay system is suitable for small GTPases in addition to K-Ras. Values are averages of quadruplicate ratios of firefly over renilla luciferase activity +/−SDs.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A kit for detection of association of a peripheral cellular membrane binding protein with cellular membranes in living cells, said kit comprising:
   a first nucleic acid construct comprising:
       a first nucleic acid molecule encoding a first fusion protein comprising a peripheral cellular membrane binding protein or membrane binding domain thereof operatively coupled to DNA binding and transactivation domains of a naturally occurring or chimeric transcription factor and
       a first promoter operatively associated with the first nucleic acid molecule and
   a second nucleic acid construct comprising:
       a second nucleic acid molecule encoding a reporter protein and
       a second promoter responsive to the DNA binding and transactivation domains of the first fusion protein, said second promoter being operatively associated with the second nucleic acid molecule, whereby activation of the second promoter results in expression of the reporter protein.

2. The kit of claim 1, wherein the first and second nucleic acid constructs are in expression vectors.

3. The kit of claim 1, wherein the peripheral cellular membrane binding protein is a K-Ras protein.

4. The kit of claim 3, wherein the transactivation domain comprises VP16.

5. The kit of claim 3, wherein the DNA binding domain comprises Gal4.

6. The kit of claim 4, wherein the VP16 is coupled to Gal4.

7. The kit of claim 1, wherein the reporter protein is a luciferase.

8. The kit of claim 1, wherein the reporter protein is a fluorescent protein.

9. The kit of claim 8, wherein the fluorescent protein is green fluorescent protein.

10. The kit of claim 1, wherein the second promoter is a multimerized UAS recognized by Gal4.

11. The kit of claim 1 further comprising:
    a control nucleic acid construct comprising:
        a third nucleic acid molecule encoding a further fusion protein comprising DNA binding and transactivation domains operatively coupled to a domain which will not bind to a cellular membrane and
        the first promoter operatively associated with the third nucleic acid molecule.

12. The kit of claim 11, wherein the first, second, and control nucleic acid constructs are in expression vectors.

13. The kit of claim 11, wherein the peripheral cellular membrane binding protein or membrane binding domain thereof is a K-Ras protein or C-terminal fragment thereof containing a "CAAX" sequence, which is modified by farnesylation, proteolysis and carboxyl methylation and thereby targets the protein to cellular membranes, while the further fusion protein is a K-ras protein lacking a "CAAX" which eliminates post-translational modification and membrane targeting.

14. The kit of claim 13, wherein the K-Ras protein lacking "CAAX" is a K-Ras protein with a C185S "SAAX" mutation.

15. A method for detection of association of a peripheral cellular membrane binding protein with a cellular membrane in living cells, said method comprising:
providing a kit comprising:
a first nucleic acid construct comprising:
a first nucleic acid molecule encoding a fusion protein comprising a peripheral cellular membrane binding protein or membrane binding domain thereof operatively coupled to DNA binding and transactivation domains of a naturally occurring or chimeric transcription factor and
a first promoter operatively associated with the first nucleic acid molecule and
a second nucleic acid construct comprising:
a second nucleic acid molecule encoding a reporter protein and
a second promoter responsive to the DNA binding and transactivation domains, said second promoter being operatively associated with the second nucleic acid molecule, whereby activation of the second promoter results in expression of the reporter protein;
transforming a first set of the living cells with the first and second nucleic acid constructs;
detecting expression of the reporter protein in the first set of transformed living cells; and
identifying the first set of transformed living cells expressing the reporter protein as having a lack of or inhibition of peripheral membrane protein association with a cellular membrane of the living cells.

16. The method of claim 15, wherein the first and second nucleic acid constructs are in expression vectors during said transforming.

17. The method of claim 15, wherein the peripheral cellular membrane binding protein is a K-Ras protein.

18. The method of claim 17, wherein the transactivation domain comprises VP16.

19. The method of claim 18, wherein the VP16 is coupled to Gal4.

20. The method of claim 15 wherein the reporter protein is a luciferase.

21. The method of claim 15 wherein the reporter protein is a fluorescent protein.

22. The method of claim 21, wherein the fluorescent protein is a green fluorescent protein.

23. The method of claim 15, wherein the second promoter is a multimerized UAS recognized by Gal4.

24. The method of claim 15, wherein said kit further comprises:
a control nucleic acid construct comprising:
a third nucleic acid molecule encoding a further fusion protein comprising DNA binding and transactivation domains operatively coupled to a domain which will not bind to a cellular membrane and
the first promoter operatively associated with the third nucleic acid molecule and, said method further comprising:
transforming a second set of the living cells with the second nucleic acid construct and the control nucleic acid construct, resulting in constitutive activation of the second promoter and constitutive expression of the reporter protein;
detecting expression of the reporter protein in the second set of transformed living cells; and
comparing expression levels of the reporter protein in the first and second sets of transformed living cells.

25. The method of claim 24, wherein the second and control nucleic acid constructs are in expression vectors.

26. The method of claim 24, wherein the peripheral cellular membrane binding protein or membrane binding domain thereof in the first fusion protein is a K-Ras protein or C-terminal fragment thereof containing a "CAAX" sequence, which is modified by farnesylation, proteolysis and carboxyl methylation and thereby targets the protein to cellular membranes, while the further fusion portion is a K-ras protein lacking a "CAAX" which eliminates post-translational modification and membrane targeting.

27. The method of claim 24 further comprising:
providing a plurality of candidate agents for inhibition of peripheral membrane protein association with a cellular membrane of the living cells;
contacting each of the plurality of candidate agents with the transformed living cells and
identifying candidate compounds which increase or decrease expression of the reporter protein as having potential application as treating conditions mediated by peripheral membrane protein association or dissociation with a cellular membrane.

28. The method of claim 27, wherein the peripheral membrane protein is K-Ras.

29. The method of claim 28, wherein the method is carried out to detect increased expression of the reporter protein and identify candidate compounds having potential application as an anti-K-Ras drug.

30. The method of claim 28, wherein the method is carried out to detect decreased expression of the reporter protein and identify candidate compounds having potential application as an anti-cancer drug.

31. The method of claim 24 further comprising:
quantifying inhibition of peripheral membrane protein association with a cellular membrane of the living cells by comparing the first and second levels.

32. The method of claim 15 further comprising:
quantifying inhibition of peripheral membrane protein association with a cellular membrane of the living cells based on reporter protein expression level.

* * * * *

```
                            SEQUENCE LISTING

<160> NUMBER OF SEQ ID NOS: 4

<210> SEQ ID NO 1
<211> LENGTH: 4
<212> TYPE: PRT
<213> ORGANISM: Artificial
<220> FEATURE:
<223> OTHER INFORMATION: CaaX motif of Ras protein
<220> FEATURE:
<221> NAME/KEY: MISC_FEATURE
<222> LOCATION: (2)..(3)
<223> OTHER INFORMATION: Any aliphatic amino acid
<220> FEATURE:
<221> NAME/KEY: MISC_FEATURE
<222> LOCATION: (4)..(4)
<223> OTHER INFORMATION: Any amino acid

<400> SEQUENCE: 1

Cys Xaa Xaa Xaa
1

<210> SEQ ID NO 2
<211> LENGTH: 4
<212> TYPE: PRT
<213> ORGANISM: Artificial
<220> FEATURE:
<223> OTHER INFORMATION: C189S mutated CaaX motif of Ras protein
<220> FEATURE:
<221> NAME/KEY: MISC_FEATURE
<222> LOCATION: (2)..(3)
<223> OTHER INFORMATION: Any aliphatic amino acid
<220> FEATURE:
<221> NAME/KEY: MISC_FEATURE
<222> LOCATION: (4)..(4)
<223> OTHER INFORMATION: Any amino acid

<400> SEQUENCE: 2

Ser Xaa Xaa Xaa
1

<210> SEQ ID NO 3
<211> LENGTH: 188
<212> TYPE: PRT
<213> ORGANISM: Homo sapiens

<400> SEQUENCE: 3

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
```

```
                     100                 105                 110
Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Glu Thr
            130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 4
<211> LENGTH: 567
<212> TYPE: DNA
<213> ORGANISM: Homo sapiens

<400> SEQUENCE: 4
atgactgaat ataaacttgt ggtagttgga gctggtggcg taggcaagag tgccttgacg      60
atacagctaa ttcagaatca ttttgtggac gaatatgatc caacaataga ggattcctac     120
aggaagcaag tagtaattga tggagaaacc tgtctcttgg atattctcga cacagcaggt     180
caagaggagt acagtgcaat gagggaccag tacatgagga ctggggaggg ctttcttgt      240 gtatttgcca taataatac taaatcattt gaagatattc accattatag agaacaaatt     300
aaaagagtta aggactctga agatgtacct atggtcctag taggaaataa atgtgatttg     360
ccttctagaa cagtagacac aaaacaggct caggacttag caagaagtta tggaattcct     420
tttattgaaa catcagcaaa gacaagacag ggtgttgatg atgccttcta tacattagtt     480
cgagaaattc gaaaacataa agaaaagatg agcaaagatg gtaaaaagaa gaaaaagaag     540
tcaaagacaa agtgtgtaat tatgtaa                                         567
```